(12) United States Patent  
Ross et al.

(10) Patent No.: US 10,078,079 B2  
(45) Date of Patent: Sep. 18, 2018

(54) DEVICE FOR DETECTING AN ANALYTE

(75) Inventors: Steve Ross, Sittingbourne (GB); Julie Richards, Sittingbourne (GB); Tim Carter, Sittingbourne (GB)

(73) Assignee: Vivacta Limited (GB)

( * ) Notice: Subject to any disclaimer, the term of this patent is extended or adjusted under 35 U.S.C. 154(b) by 265 days.

(21) Appl. No.: 14/110,033

(22) PCT Filed: Apr. 5, 2012

(86) PCT No.: PCT/GB2012/050772  
§ 371 (c)(1),  
(2), (4) Date: Dec. 16, 2013

(87) PCT Pub. No.: WO2012/137009  
PCT Pub. Date: Oct. 11, 2012

(65) Prior Publication Data  
US 2014/0119995 A1   May 1, 2014

Related U.S. Application Data

(60) Provisional application No. 61/472,886, filed on Apr. 7, 2011.

(30) Foreign Application Priority Data

Apr. 6, 2011 (GB) .................................. 1105828.6

(51) Int. Cl.  
*G01N 33/543* (2006.01)  
*G01N 21/17* (2006.01)  
(Continued)

(52) U.S. Cl.  
CPC ..... *G01N 33/54373* (2013.01); *G01N 21/171* (2013.01); *G01N 21/6428* (2013.01);  
(Continued)

(58) Field of Classification Search  
CPC ......... G01N 33/54373; G01N 21/6428; G01N 33/582; G01N 33/5302; G01N 29/022; G01N 21/171; G01N 33/542  
See application file for complete search history.

(56) References Cited

U.S. PATENT DOCUMENTS 6,743,581 B1 * 6/2004 Vo-Dinh ................ C12Q 1/001  
356/335  
8,524,504 B2   9/2013 Carter et al.  
(Continued)

FOREIGN PATENT DOCUMENTS

CN   101405602 A   4/2009  
CN   101490554 A   7/2009  
(Continued)

OTHER PUBLICATIONS

Hong Xia et al., "Preparation of Nano-scaled Magnetic Biological Probes of Fe3O4/Dextran/Antibody and Chromatographic Assay," Chemical Journal of Chinese Universities, Issue 3, pp. 445-447 (2004), abstract only.

*Primary Examiner* — Melanie Yu Brown  
(74) *Attorney, Agent, or Firm* — Wood, Phillips, Katz, Clark & Mortimer

(57) ABSTRACT

This invention relates to a device for detecting an analyte in a sample comprising: a radiation source adapted to generate a series of pulses of electromagnetic radiation; a transducer having a pyroelectric or piezoelectric element and electrodes which is capable of transducing energy generated by non-radiative decay into an electrical signal; a detector which is capable of detecting the electrical signal generated by the transducer; a first reagent proximal to the transducer, the first reagent having a binding site which is capable of binding a labelled reagent proportionally to the concentration of the analyte in the sample, which labelled reagent being capable of absorbing the electromagnetic radiation generated by the (Continued)

radiation source to generate energy by non-radiative decay; a second reagent proximal to the transducer, the second reagent having a lower affinity for the labelled reagent under the conditions of the assay than the first reagent; and a third reagent proximal to the transducer, the third reagent having a binding site which is capable of binding the labelled reagent, wherein the third reagent has an affinity for the labelled reagent which is less influenced than the first reagent by the concentration of the analyte or the complex or derivative of the analyte.

17 Claims, 8 Drawing Sheets

(51) Int. Cl.
*G01N 29/02* (2006.01)
*G01N 33/542* (2006.01)
*G01N 33/53* (2006.01)
*G01N 21/64* (2006.01)
*G01N 33/58* (2006.01)

(52) U.S. Cl.
CPC ....... *G01N 29/022* (2013.01); *G01N 33/5302* (2013.01); *G01N 33/542* (2013.01); *G01N 33/582* (2013.01); *G01N 2021/6439* (2013.01); *G01N 2201/062* (2013.01); *G01N 2291/0255* (2013.01); *G01N 2291/0256* (2013.01); *G01N 2291/02433* (2013.01)

(56) References Cited

U.S. PATENT DOCUMENTS

| | | | |
|---|---|---|---|
| 9,057,723 B2 | 6/2015 | Carter et al. | |
| 2004/0005582 A1* | 1/2004 | Shipwash | 435/6 |
| 2004/0065832 A1* | 4/2004 | Cluff | G01N 21/3581 250/341.1 |
| 2004/0081969 A1* | 4/2004 | Ilsley | G01N 33/543 506/9 |
| 2005/0255491 A1* | 11/2005 | Lee | B82Y 5/00 435/6.18 |
| 2006/0263894 A1* | 11/2006 | Carter | G01N 21/1702 436/149 |
| 2009/0087862 A1 | 4/2009 | Carter et al. | |
| 2009/0203154 A1 | 8/2009 | Carter et al. | |
| 2010/0041563 A1* | 2/2010 | Li et al. | 506/9 |
| 2012/0283122 A1* | 11/2012 | Lea | G01N 33/6845 506/9 |

FOREIGN PATENT DOCUMENTS

| | | |
|---|---|---|
| CN | 101815942 A | 8/2010 |
| CN | 101981449 A | 2/2011 |
| JP | 2010-197248 A | 9/2010 |
| WO | 2004/090512 A1 | 10/2004 |
| WO | 2010/004241 A1 | 1/2010 |

* cited by examiner

DEVICE FOR DETECTING AN ANALYTE

This application is a National Phase of International Application Serial No. PCT/GB2012/050772, filed Apr. 5, 2012, which claims priority of U.S. Provisional Patent Application No. 61/472,886, filed on Apr. 7, 2011 and United Kingdom Patent Application No. 1105828.6, filed on Apr. 6, 2011, which are incorporated herein by reference in their entireties.

The present invention relates to a device for detecting an analyte, and particularly to improving accuracy and precision in a device incorporating a piezo/pyroelectric transducer.

The monitoring of analytes in solution, such as biologically important compounds in bioassays, has a broad applicability. Accordingly, a wide variety of analytical and diagnostic devices are available.

WO 90/13017 discloses a pyroelectric or other thermoelectric transducer element in a strip form. Thin film electrodes are provided and one or more reagents are deposited on the transducer surface. The reagent undergoes a selective colorimetric change when it comes into contact with the species being detected. The device is then typically inserted into a detector where the transducer is illuminated usually through the transducer by an LED light source and light absorption by the reagent is detected as microscopic heating at the transducer surface. The electrical signal output from the transducer is processed to derive the concentration of the species being detected.

WO 2004/090512 discloses a device based on the technology disclosed in WO 90/13017, but relies on the finding that energy generated by non-radiative decay in a substance on irradiation with electromagnetic radiation may be detected by a transducer even when the substance is not in contact with the transducer, and that the time delay between the irradiation with electromagnetic radiation and the electrical signal produced by the transducer is a function of the distance of the substance from the surface of the film. This finding provided a device capable of "depth profiling" which allows the device to distinguish between an analyte bound to the surface of the transducer and an analyte in the bulk liquid. This application therefore discloses a device which is able to be used in assays, typically bioassays, without having to carry out a separate washing step between carrying out a binding event and detecting the results of that event (termed a "homogeneous" assay).

The system described in WO 90/13017 and WO 2004/090512 uses a piezo/pyroelectric transducer to measure binding events. The binding events take place at the surface of the transducer, and the measurement process is initiated by pulsing electromagnetic radiation (light) into the system. Light absorption causes localised heating of a labelled reagent which, in turn generates an electric charge in the transducer. The electrical output can be interrogated in such a fashion as to distinguish between the bound and unbound reagent, and hence characterise the amount of analyte in a fluid sample. The rate of binding to the surface in situ can be determined without separation steps.

Any measurement process will suffer from imprecision or inaccuracy in the measurement owing to natural variations in the components which make up the system. There may also be interference in the measurement process from environmental factors, such as temperature or humidity. Measurements which are carried out in bodily fluids, such as blood or plasma, may also be affected by the composition of those fluids. This may be due to interfering factors, such as lipids, bilirubin and heterophilic antibodies, or due to natural variations in viscosity, hematocrit, etc.

It is common in laboratory analysers to run calibrations at regular intervals, which confirm that the instrument is performing appropriately, and also to calibrate the instrument. This calibration process improves the measurement process by adjusting the system for variability in the components from different batches.

However, in the system described in WO 90/13017 and WO 2004/090512, the kinetic binding of a labelled reagent to the sensor surface is monitored in situ by monitoring the rate of change of signal over time in the presence of the analyte (or a complex or derivative of the analyte) to be measured. This is different to other immunoassay systems which often measure some form of equilibrium position that has been achieved after an incubation period of a predetermined length. In addition, since the system described in WO 90/13017 and WO 2004/090512 can measure the labelled reagent relative to the sensor surface, unwanted movement of the labelled reagent, or indeed other particles in the measurement chamber, can interfere with the signal measurement. There, therefore, remains a need for systems providing improved accuracy and precision.

Accordingly, the present invention provides a device for detecting an analyte in a sample comprising:

a radiation source adapted to generate a series of pulses of electromagnetic radiation;

a transducer having a pyroelectric or piezoelectric element and electrodes which is capable of transducing energy generated by non-radiative decay into an electrical signal;

a detector which is capable of detecting the electrical signal generated by the transducer;

a first reagent proximal to the transducer, the first reagent having a binding site which is capable of binding a labelled reagent proportionally to the concentration of the analyte in the sample, which labelled reagent being capable of absorbing the electromagnetic radiation generated by the radiation source to generate energy by non-radiative decay;

a second reagent proximal to the transducer, the second reagent having a lower affinity for the labelled reagent under the conditions of the assay than the first reagent; and a third reagent proximal to the transducer, the third reagent having a binding site which is capable of binding the labelled reagent, wherein the third reagent has an affinity for the labelled reagent which is less influenced than the first reagent by the concentration of the analyte or the complex or derivative of the analyte.

Thus, the present invention provides a device for detecting an analyte which incorporates both positive (third reagent) and negative (second reagent) controls to improve the accuracy and precision in the detection (via the first reagent).

The present invention will now be described with reference to the drawings, in which.

Figure 13:
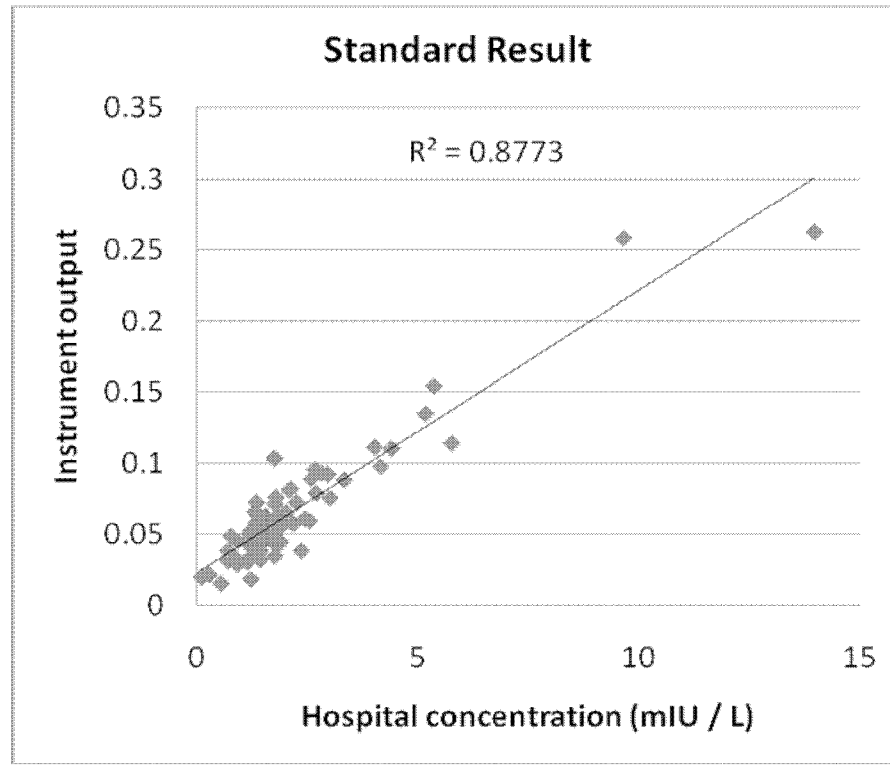
Figure 14:
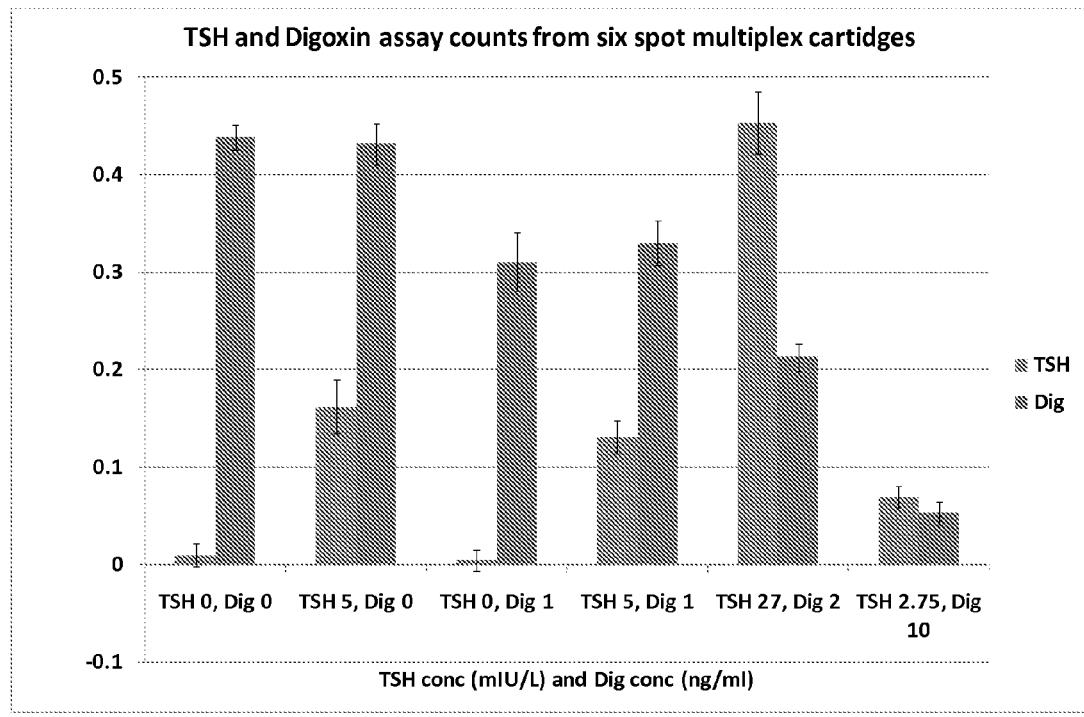

FIGS. 10-13 show a TSH assay in whole blood using no control, negative control only, positive control only and both controls, respectively; and FIG. 14 shows instrument outputs for simultaneous determination of TSH and digoxin levels using the same controls for each assay The device of the present invention is used for detecting an analyte in a sample (which may be via the detection of a complex or derivative of the analyte). The device comprises: a radiation source adapted to generate a series of pulses of electromagnetic radiation; a transducer having a pyroelectric or piezoelectric element and electrodes which is capable of transducing energy generated by non-radiative decay into an electrical signal; and a detector which is capable of detecting the electrical signal generated by the transducer. In a preferred embodiment, the device of the present invention is based on the device described in WO 2004/090512.

Figure 1:
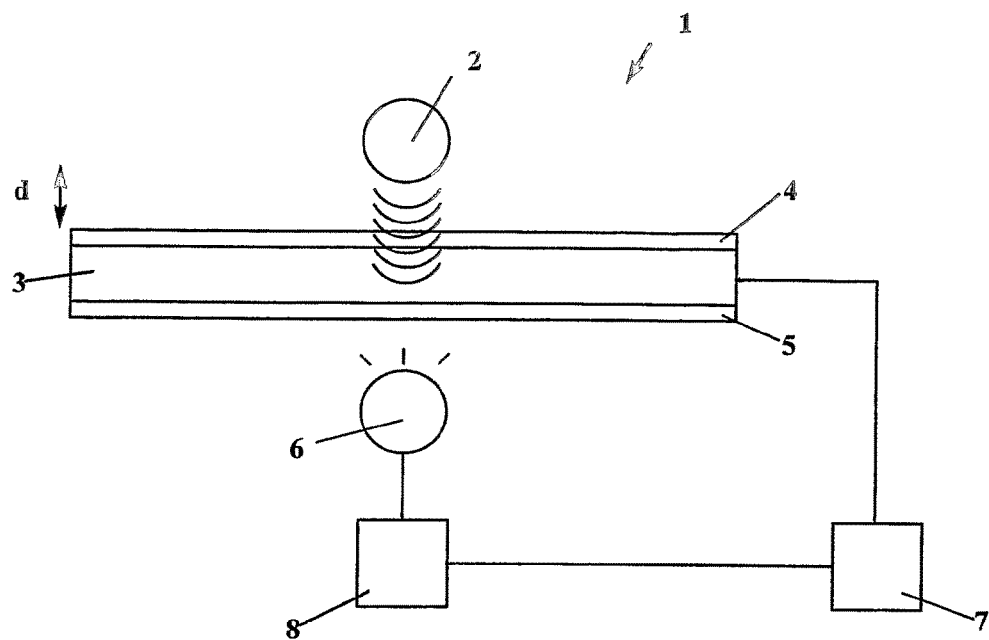
FIG. 1 shows a schematic representation of the chemical sensing device of WO 2004/090512 which is used with the present invention.

FIG. 1 shows a chemical sensing device 1 for use in accordance with the present invention which relies on heat generation in a label 2 on irradiation of the label 2 with electromagnetic radiation. For the sake of simplicity, only the label is shown in FIG. 1 (the remaining components of the device of the present invention will be described in further detail hereinbelow). FIG. 1 shows the chemical sensing device 1 in the presence of a label 2. The device 1 comprises a pyroelectric or piezoelectric transducer 3 having electrode coatings 4,5. The transducer 3 is preferably a poled polyvinylidene fluoride film. The electrode coatings 4,5 are preferably transparent and most preferably formed from indium tin oxide. The electrodes preferably have a thickness of about 35 nm, although almost any thickness is possible from a lower limit of 1 nm below which the electrical conductivity is too low and an upper limit of 100 nm above which the optical transmission is too low (it should not be less than 80% T). In a particularly preferred embodiment, the transducer is an indium tin oxide-coated polyvinylidene fluoride film.

The label 2 is held proximal to the transducer 3 by a binding event. A preferred feature of the present invention is that the label 2 generates heat when irradiated by a source of electromagnetic radiation (typically termed "light") 6, preferably visible light. The light source may be, for example, an LED. The light source 6 illuminates the label 2 with light of the appropriate wavelength (e.g. a complementary colour). Although not wishing to be bound by theory, it is believed that the label 2 absorbs the light to generate an excited state which then undergoes non-radiative decay thereby generating energy, indicated by the curved lines in FIG. 1. This energy is primarily in the form of heat (i.e. thermal motion in the environment) although other forms of energy, e.g. a shock wave, may also be generated. The energy is, however, detected by the transducer and converted into an electrical signal. The device of the present invention is calibrated for the particular label being measured and hence the precise form of the energy generated by the non-radiative decay does not need to be determined. Unless otherwise specified the term "heat" is used herein to mean the energy generated by non-radiative decay. The light source 6 is positioned so as to illuminate the label 2. Preferably, the light source 6 is positioned opposite the transducer 3 and electrodes 4,5 and the label 2 is illuminated through the transducer 3 and electrodes 4,5. The light source may be an internal light source within the transducer in which the light source is a guided wave system. The wave guide may be the transducer itself or the wave guide may be an additional layer attached to the transducer. The wavelength of illumination depends on the label used; for example, for 40 nm gold labels the preferred wavelength is 525 nm and for carbon labels the preferred wavelength is 690 nm.

The energy generated by the label 2 is detected by the transducer 3 and converted into an electrical signal. The electrical signal is detected by a detector 7. The light source 6 and the detector 7 are both under the control of the controller 8. The light source 6 generates a series of pulses of light (the term "light" used herein means any form of electromagnetic radiation unless a specific wavelength is mentioned) which is termed "chopped light". In principle, a single flash of light, i.e. one pulse of electromagnetic radiation, would suffice to generate a signal from the transducer 3. However, in order to obtain a reproducible signal, a plurality of flashes of light are used which in practice requires chopped light. The frequency at which the pulses of electromagnetic radiation are applied may be varied. At the lower limit, the time delay between the pulses must be sufficient for the time delay between each pulse and the generation of an electrical signal to be determined. At the upper limit, the time delay between each pulse must not be so large that the period taken to record the data becomes unreasonably extended. Preferably, the frequency of the pulses is from 1-50 Hz, more preferably 1-10 Hz and most preferably 2 Hz. This corresponds to a time delay between pulses of 20-1,000 ms, 100-1,000 ms and 500 ms, respectively. In addition, the so-called "mark-space" ratio, i.e. the ratio of on signal to off signal is preferably one although other ratios may be used without deleterious effect. There are some benefits to using a shorter on pulse with a longer off signal, in order to allow the system to approach thermal equilibrium before the next pulse perturbs the system. In one embodiment, a light pulse of 1-50 ms, preferably 8 ms, followed by a relaxation time of 10-500 ms, preferably 100 ms allows a more precise measurement of particles bound directly to the surface. Sources of electromagnetic radiation which produce chopped light with different frequencies of chopping or different mark-space ratios are known in the art. The detector 7 determines the time delay between each pulse of light from light source 6 and the corresponding electrical signal detected by detector 7 from transducer 3. The applicant has found that this time delay is a function of the distance, d. The signal is preferably measured from 2-7 ms.

Any method for determining the time delay between each pulse of light and the corresponding electrical signal which provides reproducible results may be used. Preferably, the time delay is measured from the start of each pulse of light to the point at which a maximum in the electrical signal corresponding to the absorption of heat from bound label is detected as by detector 7.

The finding that the label 2 may be separated from the transducer surface and that a signal may still be detected was surprising since the skilled person would have expected the heat to be dispersed into the surrounding medium and hence be undetectable by the transducer 3 or at least for no meaningful signal to be received by the transducer. It was found, surprisingly, that not only was the signal detectable through an intervening medium capable of transmitting energy to the transducer 3, but that different distances, d, may be distinguished (this has been termed "depth profiling") and that the intensity of the signal received is proportional to the concentration of the label 2 at the particular distance, d, from the surface of the transducer 3. Moreover, it was found that the nature of the medium itself influences the time delay and the magnitude of the signal at a given time delay.

The device of the present invention has particular applicability in performing immunoassays.

In a typical immunoassay, an antibody specific for an antigen of interest is attached to a polymeric support such as a sheet of polyvinylchloride or polystyrene. A drop of cell extract or a sample of serum or urine is laid on the sheet, which is washed after formation of the antibody-antigen complex. Antibody specific for a different site on the antigen is then added, and the sheet is again washed. This second antibody carries a label so that it can be detected with high sensitivity. The amount of second antibody bound to the sheet is proportional to the quantity of antigen in the sample. This assay and other variations on this type of assay are well known, see, for example, "The Immunoassay Handbook, 2nd Ed." David Wild, Ed., Nature Publishing Group, 2001. The device of the present invention may be used in any of these assays. Sandwich, competitive, displacement and anticomplex antibody immunoassays also warrant particular mention.

Figure 2:
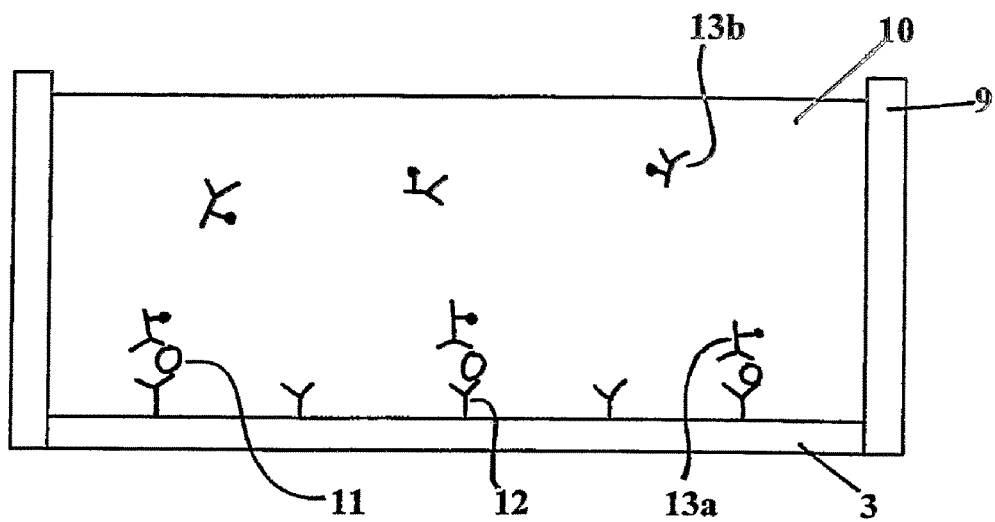
FIG. 2 shows a sandwich immunoassay using the device of the present invention.

By way of an explanation of the principle underlying the present invention, FIG. 2 shows a typical capture antibody assay using the device of the present invention (although only the first reagent is shown). The device includes a transducer 3 and a sample chamber 9 for holding a liquid 10 containing an analyte 11 dissolved or suspended therein. The transducer 3 has a first reagent, i.e. antibody 12, attached thereto. The first reagent 12 is shown attached to the film in FIG. 2 and this attachment may be via a covalent bond or by non-covalent adsorption onto the surface, such as by hydrogen bonding. Although the first reagent is shown as attached to the transducer, any technique for holding the first reagent 12 proximal to the transducer 3 is applicable. For example, an additional layer may separate the first reagent 12 and the transducer 3, such as a parylene polymer layer, or the antibody could be attached to inert particles and the inert particles are then attached to the transducer 3. Alternatively, the first reagent 12 could be entrapped within a gel layer which is coated onto the surface of the transducer 3.

In use, the sample chamber is filled with liquid 10 (or any fluid) containing an analyte 11. The analyte 11 then binds to first reagent 12. Additional labelled reagent 13 is present in the liquid and a so-called "sandwich" complex is formed between the bound first reagent 12, the analyte 11 and the labelled reagent 13. An excess of labelled reagent 13 is included so that all of the bound antigen 11 forms a sandwich complex. The sample therefore contains bound labelled reagent 13a and unbound labelled reagent 13b free in solution.

During or following formation of the sandwich complex, the sample is irradiated using a series of pulses of electromagnetic radiation, such as light. The time delay between each pulse and the generation of an electrical signal by the transducer 3 is detected by a detector. The appropriate time delay is selected to measure primarily the heat generated by the bound labelled reagent 13a. Since the time delay is a function of the distance of the label from the transducer 3, the bound labelled reagent 13a may be distinguished from the unbound labelled reagent 13b. This provides a significant advantage over the conventional sandwich immunoassay in that it removes the need for washing steps. In a conventional sandwich immunoassay, the unbound labelled reagent must be separated from the bound labelled reagent before any measurement is taken since the unbound labelled reagent interferes with the signal generated by the bound labelled reagent. However, on account of the "depth profiling" provided by the present invention, bound and unbound labelled reagent may be distinguished. Indeed, the ability to distinguish between labels proximal to the transducer (i.e. bound) and labels in the bulk solution (i.e. unbound) is a particular advantage of the present invention.

The present invention also provides a method for detecting an analyte, or a complex or derivative of the analyte, in a sample comprising the steps of exposing the sample to the device as described herein, transducing the energy generated into an electrical signal and detecting the signal. Preferably, the method is carried out without removing the sample from the transducer between the steps of exposing the sample to the transducer and transducing the energy generated into an electrical signal, i.e. the method is a homogeneous assay.

The present invention provides controls which compensate for natural variability in the components of the measuring system, variability in the samples that are measured, and variability in the environmental conditions during the measurement. This can be achieved by exposing the sample to reagents on the surface of the transducer. The different reagents are typically located at different areas of the transducer surface, these areas being coated in different reagents. These controls are defined as "negative" and "positive" controls, in the sense that the negative control should approximate the expected signal in the absence of analyte, and the positive control should approximate the expected signal when analyte has saturated the system.

To achieve detection with these controls, the device of the present invention comprises a first, second and third reagent, each of which is proximal to the transducer.

The first reagent has a binding site which is capable of binding a labelled reagent proportionally to the concentration of the analyte in the sample. The proportionality is important for the functioning of the assay since the binding must be dependent on the concentration of the analyte for any meaningful measure of the concentration of the analyte to be determined. The binding may be directly proportional or indirectly proportional to the concentration of the analyte depending on the type of assay being performed. In the case of a non-competitive assay, e.g. an immunometric assay, the binding is directly proportional to the concentration of the analyte, but for a competitive assay, the binding is indirectly proportional to the concentration of the analyte.

The first reagent may be adapted to bind to the analyte, or a complex or derivative of the analyte, in which case the labelled reagent will bind to the first reagent in the presence of the analyte, or the complex or derivative of the analyte. In this case, the first reagent has a binding site which is capable of binding to the labelled reagent in the presence of the analyte or the complex or derivative of the analyte. The binding is, however, still proportional to the concentration of the analyte.

Alternatively, the first reagent may itself be an analogue of the analyte and the labelled reagent binds directly to the first reagent (it is an analogue because it is bound to the transducer surface either through covalent bonding or non-covalent interactions). In this case, the first reagent will compete with the unbound analyte, or an unbound complex or derivative of the analyte, for the binding of the labelled reagent. Accordingly, the first reagent will simply be capable of binding to the labelled reagent Determining the extent of binding of the labelled reagent to the first reagent (either directly or mediated by the analyte/complex or derivative of the analyte) provides a measurement of the concentration of the analyte in the sample The second reagent has a lower affinity for the labelled reagent under the conditions of the assay than the first reagent. Accordingly, the second reagent provides the negative control. It is important that the affinity is considered under the conditions of the assay. The reason is that in the case of a non-competitive assay, the affinity of the first reagent for the labelled reagent is mediated by the presence of the analyte, or the complex or derivative of the analyte. Thus, in the absence of the analyte, or the complex or derivative of the analyte, neither the first nor second reagent has any affinity for the labelled reagent. However, in the presence of the analyte, or the complex or derivative of the analyte, the second reagent has a lower affinity for the labelled reagent than the first reagent.

In addition, in the embodiments where the first reagent binds to the analyte, or the complex or derivative of the analyte, the second reagent preferably has a lower affinity for the analyte or, if used, the complex or derivative of the analyte than the first reagent. The second reagent is preferably a protein and more preferably an antibody. The second reagent typically has similar chemical and physical properties to the first reagent, but provides little or no affinity for the labelled reagent under the conditions of the assay. In a particularly preferred embodiment, the second reagent has essentially no affinity for the labelled reagent under the conditions of the assay. Preferably, second reagent provides essentially no affinity for the analyte or the complex or derivative of the analyte. That is, the binding of the labelled reagent, or, where applicable, the analyte or the complex or derivative of the analyte, to the second reagent is non-specific. In this manner, the second reagent can compensate for non-specific binding of the labelled reagent to the first reagent, and can also compensate for unwanted movement of the labelled reagent relative to the transducer, e.g. by sedimentation under gravity, which can interfere with the measurement process.

The third reagent binds to the labelled reagent and has an affinity for the labelled reagent which is less influenced by the concentration in the sample of the analyte or, if used, the complex or derivative of the analyte than the first reagent and hence provides the positive control. Preferably, the third reagent has an affinity for the labelled reagent which is essentially independent of the concentration of the analyte or the complex or derivative of the analyte. More preferably, the third reagent has a higher affinity for the labelled reagent under the conditions of the assay than the first reagent. In this manner, the third reagent measures the diffusion-limited rate of binding of the labelled reagent to the transducer and hence determines the maximum signal obtainable under diffusion. At extremely high concentrations of the analyte or the complex or derivative of the analyte, concentration effects may be seen, but provided the affinity is less influenced by the concentration than that of the first reagent, the third reagent can still provide a positive control even at high concentrations.

By interrogating the output of the detector, a ratiometric signal can be obtained which defines the magnitude of the signal from binding to the first reagent (i.e. the measurement signal) relative to the binding of the second and third reagents (i.e. the negative and positive controls, respectively) as a fractional output between 0.000 and 1.000.

The first, second and third reagents may be attached to the transducer using techniques known in the art. Preferably the attachment is via non-covalent bonding, for example, a primary layer is adsorbed on to the transducer and the reagents are attached to the primary layer by a binding event.

The assay also requires the presence of a labelled reagent. By "labelled" reagent is meant a reagent which is attached to a label, which label being capable of absorbing the electromagnetic radiation generated by the radiation source to generate energy by non-radiative decay. It is this non-radiative decay which is transduced into an electrical signal by the transducer.

The label may therefore be composed of any material which is capable of interacting with the electromagnetic radiation in this manner. Preferably the label is selected from, but not limited to, a carbon particle, a coloured-polymer particle (e.g. coloured latex), a dye molecule, an enzyme, a fluorescent molecule, a metal (e.g. gold) particle, a haemoglobin molecule, a red blood cell, a magnetic particle, a nanoparticle having a non-conducting core material and at least one metal shell layer, a particle composed of polypyrrole or a derivative thereof, and combinations thereof. Preferably, the label is a carbon particle or a gold particle and most preferably a carbon particle.

In the case of a magnetic particle, the electromagnetic radiation is radio frequency radiation. All of the other labels mentioned hereinabove employ light, which can include IR or UV radiation. Gold particles are commercially available or may be prepared using known methods (see for example G. Frens, Nature, 241, 20-22 (1973)). For a more detailed explanation of the nanoparticle label see U.S. Pat. No. 6,344,272 and WO 2007/141581.

Preferably, the present invention uses a particle having a particle size of 20 to 1,000 nm, more preferably 100 to 500 nm. By particle size is meant the diameter of the particle at its widest point. The density of the particle will depend on the type of assay. Where the assay is diffusion-controlled, the particle preferably has a density of 0.5 to 3.0 g/mL, more preferably 1.5-2.0 g/mL and most preferably 1.8 g/mL. In this assay type, the particle is a carbon particle having the aforementioned particle size and density. Where the assay is gravity-assisted, the particle preferably has a density of 1.5 to 23 g/mL, more preferably 15-20 g/mL and most preferably 19 g/mL. In this assay type, the particle is a gold particle having the aforementioned particle size and density.

The label is proximal to the transducer when the binding event has occurred. That is, the label is sufficiently close to the surface of the transducer for the transducer to be able to detect the energy generated by the label on irradiation of the sample. The actual distance between the label and the surface of the transducer will, however, depend on a number of variables, such as the size and nature of the label, the size and nature of the antibodies and the analyte, the nature of the sample medium, and the nature of the electromagnetic radiation and the corresponding settings of the detector. The device of the present invention may include a radiation source which is adapted to generate a series of pulses of electromagnetic radiation and the detector is adapted to determine the time delay between each pulse of electromagnetic radiation from the radiation source and the generation of the electric signal thereby allowing a precise determination of the position of the label with respect to the transducer as discussed with reference to FIG. 1.

The nature of the first, second and third reagents, as well as the labelled reagent, will depend on the nature of the analyte, but they are preferably antibodies. In a particularly preferred embodiment, the labelled reagent comprises an antibody raised to the analyte or the complex or derivative of the analyte, the first reagent is an antibody raised to the analyte or the complex or derivative of the analyte, the second reagent is an isotype control antibody, and the third reagent is an anti-species antibody. In principle, a single molecule could be used for each reagent, but in practice, the first, second and third reagents, as well as the labelled reagent, are a population of molecules. The term "antibody" preferably includes within its scope a Fab fragment, a single-chain variable fragment (scFv), and a recombinant binding fragment.

In a preferred embodiment, particularly but not limited to where the reagents are antibodies, the affinity constant of the third reagent is $\geq 10^7$ $dm^3mol^{-1}$, more preferably $\geq 10^8$ $dm^3mol^{-1}$. The affinity may be determined using the Scatchard equation with the absorbance measured in an ELISA, a common method for determining antibody affinities, as described in "Immunoassays" Ed. J. P. Gosling, Oxford University Press, 2000, pages 80-83. The second reagent preferably has an affinity such that the kinetic binding rate is ≤10% of the third reagent and more preferably ≤5%.

As alternatives to antibody-antigen reactions, the reagents and analyte may be a first and second nucleic acid where the first and second nucleic acids are complementary, or a reagent containing avidin or derivatives thereof and an analyte containing biotin or derivatives thereof, or vice versa. The reagents may also be aptamers. The system is also not limited to biological assays and may be applied, for example, to the detection of heavy metals in water. The system also need not be limited to liquids and any fluid system may be used, e.g. the detection of enzymes, cells and viruses etc. in the air.

The maximum observable signal is the maximum signal that can be achieved when monitoring the label binding to a surface. In the absence of alternative mass transport phenomena (e.g. convection, magnetic movement, buoyancy, sedimentation, etc.), the binding of particles to the transducer is governed by the diffusion rate of the analyte and labelled reagent which is, in turn, governed largely by the hydrodynamic radius of these components and the viscosity/temperature of the sample. The negative and positive controls should give signals that are independent of the absence or presence of the analyte to be measured.

It has been found that for immunometric (i.e. sandwich or reagent-excess) assays, improvements in performance can be achieved by using an anti-species antibody as the positive control (that recognises an anti-analyte antibody on the labelled reagent), and a non-reactive isotype control antibody (or simply a non-reactive surface) as the negative control. When used in combination, these controls define the upper and lower limits of the measuring range of the system. Thus, the output from the system is defined as the ratio of where the measurement lies between these two limits. Surprisingly this combination can be used to account for variations in the system components (e.g. the material forming the transducer), the environmental conditions, the sample variability and unwanted particle movement (e.g. sedimentation) in combination. The controls provided by the present invention have been found to compensate for all these parameters at the same time.

If a molecule is sufficiently small that formation of an antibody sandwich is not achievable, different types of assay need to be considered. One class of assay for small molecules is the "competitive assay", in which the analyte of interest competes with another component in the system to prevent binding. In competitive assays the signal is inversely related to the analyte concentration. One particular type of assay is presented in which an antibody to the analyte is immobilised on the transducer, and a labelled analogue of the analyte is introduced into the sample. The analyte and labelled analogue of the analyte then "compete" for the antibody on the surface. In the absence of analyte, then the labelled analogue will bind at the maximum possible rate. However, in the presence of analyte, the antibody on the transducer becomes populated with analyte and the rate of binding of the analogue is diminished. The present invention has applicability to such assays in which the controls reduce variability in the system.

Incorporation of the analogue of the analyte onto the particle can be achieved by first attaching the analogue to a carrier to form an analogue-carrier conjugate, and then attaching the conjugate to the surface of the label. The carrier is preferably a protein, a polysaccharide or a synthetic polymer. The attachment of the analogue to the carrier is preferably by covalent bonding. The attachment of the conjugate to the surface of the carrier is preferably achieved by adsorbing the conjugate to the surface of the label. One approach to mimic maximum binding rate is to use a third reagent on the transducer surface which recognises the carrier, e.g. an antibody raised to the carrier protein. However, the rate of binding in this control may be suboptimal, because the analogue can mask the surface of the carrier, making it sterically hindered. The relative populations of carrier and analogue on the particle could also be quite different.

Thus, for competitive assays, the labelled reagent preferably comprises a label having a carrier attached thereto, wherein the carrier has two different molecules attached thereto. The first molecule is an analogue of the analyte and the second molecule is unrelated, but of similar size to the analogue/analyte. The two different molecules would preferably be conjugated to the carrier in a 1:1 molar ratio to each other. The third reagent would then bind the labelled reagent at a similar rate to the second reagent in the absence of analyte.

The labelled reagent for use in such an assay (i.e. a competitive assay) has been specifically designed for use with the device of the present invention. Thus, the present invention further provides a labelled reagent comprising a label capable of absorbing electromagnetic radiation to generate energy by non-radiative decay, a carrier attached to the label, and attached to the carrier, a first member of a first complementary binding pair and a first member of a second complementary binding pair. The first member of the first complementary binding pair is an analogue of the analyte to be detected and hence the second member of the first complementary binding pair will be the first reagent, for example, an antibody raised to the analyte. The first member of the second complementary binding pair is a molecule which is not normally found in the sample, and which is capable of binding to the third reagent. The second member of the second complementary binding pair will be the third reagent. The carrier is preferably a protein. The first and second complementary binding pairs are different, in the sense that the first and second members of the respective pairs would not have any affinity for one another. By way of an example, the analyte is the drug digoxin, the label is a carbon particle, the carrier is bovine serum albumin, the first member of the first complementary binding pair is digoxigenin (an analogue of digoxin), the second member of the first complementary binding pair is an anti-digoxin antibody, the first member of the second complementary binding pair is fluorescein isothiocyanate and the second member of the second complementary binding pair is an anti-fluorescein antibody.

Examples of the first member of the first complementary binding pair are therapeutic drugs (e.g. carbamazepine, cyclosporine, digoxin, theophylline and gentamycin), drugs of abuse (e.g. opiates, cocaine and amphetamine), vitamins (e.g. vitamin D, vitamin B12 and folate) and hormones (T3, T4, cortisol, progesterone, estradiol and testosterone); and examples of the first member of the second complementary binding pair are BODIPY FL, Dansyl, AlexaFluor 405, AlexaFluor 488, Lucifer Yellow, Rhodamine, Texas Red, biotin (unless used for immobilisation of the first, second and/or third reagents) and dinitrophenyl aminohexanoic acid.

In order to increase the dynamic range of an assay performed in accordance with the present invention, whilst also improving precision, it is preferred to have the first reagent in a plurality of locations on the transducer. These locations may be tuned to different sensitivities, by varying the concentration of the first reagent at each location. Each location may also have its own second and third reagents to act as controls for the different dynamic ranges. This is particularly applicable to competitive assays which are particularly sensitive to the concentration of each of the individual components which make up the system.

The device may also have a plurality of locations as described hereinabove, and the labelled reagent also has two different binding sites. In this instance the analyte blocks one site on the label in one location, but this does not inhibit binding to the reagent in the control.

The analyte may be a macromolecule or a small molecule. The macromolecule is typically a protein, such as a protein-based hormone, and may also be part of a larger particle, such as a virus, a bacterium, a cell (e.g. a red blood cell) or a prion. The small molecule may be a drug.

The term "small molecule" used herein is a term of the art and is used to distinguish the molecule from macromolecules such as proteins and nucleic acids. A small molecule is often referred to in the field of immunoassays as a "hapten", being a small molecule which, when attached to a large carrier molecule such as a protein, can elicit an immune response and includes molecules such as hormones and synthetic drugs. A small molecule of this type will typically have a molecular weight of 2,000 or less, often 1,000 or less and even 500 or less. The first reagent may be adapted to bind to the analyte itself, although the analyte can undergo a chemical reaction or initial complexing event before binding to the first reagent. For example, the analyte might be protonated/deprotonated in the pH of the assay conditions. Thus, the analyte which is bound to the first reagent may be analyte itself or a derivative of the analyte; both are included within the scope of the present invention.

In a preferred embodiment, the present invention may be used to detect the presence of a small molecule and a macromolecule in the same sample at the same time. That is, the sample includes at least two analytes, one being a small molecule and one being a macromolecule. At least two first reagents are used, one to bind to the small molecule in a competitive assay and one to bind to the macromolecule in an immunometric assay. The second and third reagents are preferably the same, i.e. the positive and negative controls are the same for both assay types.

Figure 3:
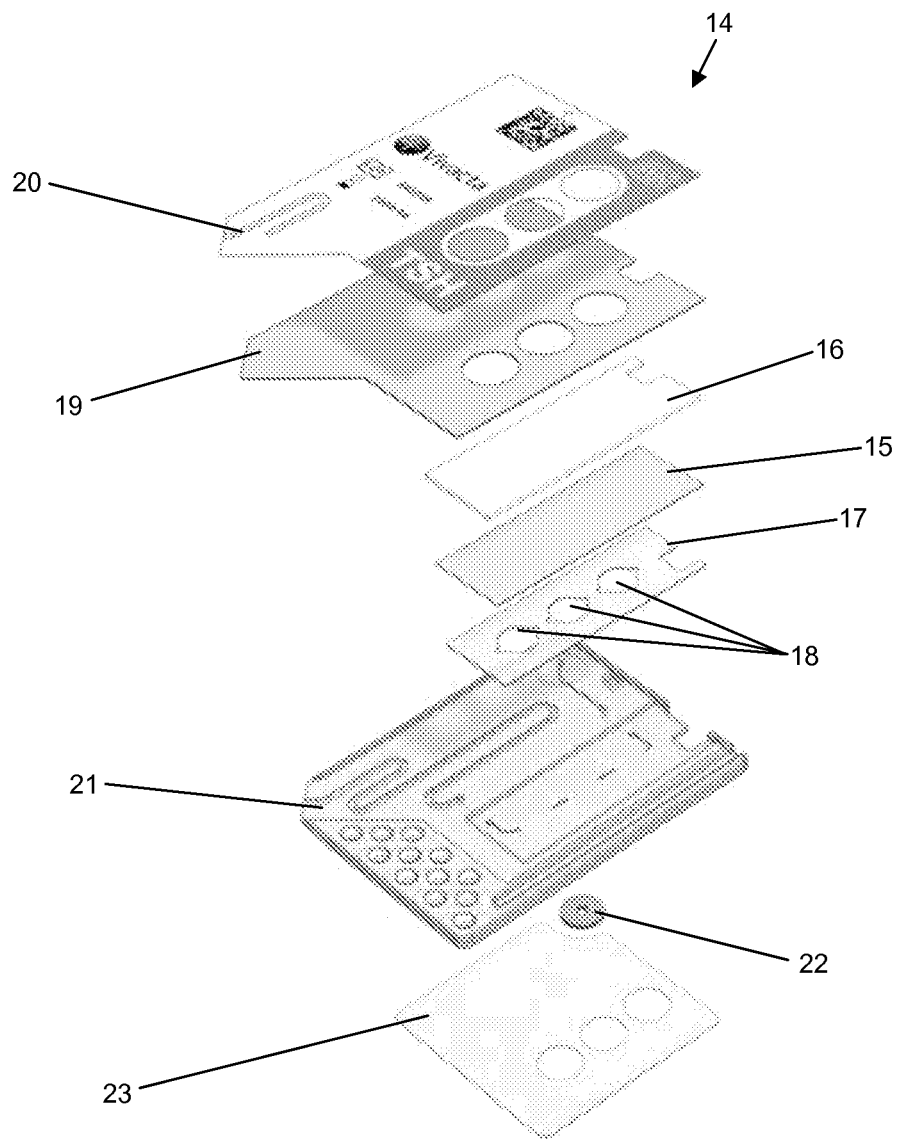
FIG. 3 shows a cartridge according to the present invention.

The sample which is suspected of containing the analyte of interest will generally be a fluid sample, e.g. a liquid sample, and usually a biological sample, such as a bodily fluid, e.g. blood, plasma, saliva, serum or urine. The sample may contain suspended particles and may even be whole blood. An advantage of the method of the present invention is that the assay may be performed on a sample which does contain suspended particles without unduly influencing the results of the assay. The sample will typically be in the order of microliters (e.g. 1-100 µL, preferably 1-10 µL). In order to hold a fluid sample, the transducer is preferably located in a sample chamber having one or more side walls, an upper surface and a lower surface. Accordingly, the device of the present invention preferably further comprises a chamber for holding a liquid sample containing the analyte or the complex or derivative of the analyte in contact with the transducer. In a preferred embodiment, the transducer is integral with the chamber, i.e. it forms one of the side walls, or upper or lower surface which define the chamber. Preferably the transducer forms the upper surface as shown in FIG. 3. Clearly, the first, second and third reagents and the labelled reagent will be on the interior surfaces of the chamber to allow contact with the sample. The sample may simply be retained by surface tension forces, for example, inside a capillary channel.

The device preferably contains a first chamber containing the first reagent, a second chamber containing the second reagent and a third chamber containing the third reagent. The first, second and third chambers are preferably in fluid communication. The device preferably further contains a capillary channel having a sample receiving end which is contact with the outside of the device and a sample delivery end which is in fluid communication with the sample chamber(s), as shown in the core 21 in FIG. 3.

The labelled reagent and optionally one or more additional reagents are preferably stored in a chamber incorporated into the device of the present invention. The labelled reagent may also be supplied as part of kit incorporating the device and the labelled reagent. Accordingly, the present invention also provides a kit comprising the device as described herein and the labelled reagent. The labelled reagent may be deposited onto the surface of the transducer.

The device of the present invention is not restricted to detecting only one analyte and different analytes may be detected by employing different first reagents which selectively bind each analyte, or a derivative or complex of the analyte, being detected. Multiple tests can be carried out using only one electrical connection to the transducer, by illuminating different locations of the transducer sequentially and interrogating the outputs sequentially.

A potential additional source of background interference is the settling of suspended particles on to the surface of the piezo/pyroelectric transducer, including labelled reagent and cellular components of the sample. This source of interference may be reduced by positioning the transducer above the bulk solution, e.g. on the upper surface of the reaction chamber. Thus, if any settling occurs, it will not interfere with the transducer. Alternatively, the particles could be less dense than the medium and hence float to the surface of the bulk solution rather than settling on the surface of the transducer. This and other modifications are included in the scope of the present invention.

In a preferred embodiment, the device of the present invention consists essentially of the above-described features. By "essentially" is meant that no other features are required to perform the assay. The device may take the form of a separate reader and cartridge, or an integrated device. In the former, the device is formed of a reader and a cartridge, in which the cartridge is releasably engageable with the reader, and in which the reader incorporates the radiation source and the detector, and the cartridge incorporates the transducer and the first, second and third reagents. The reader is preferably a portable reader. The present invention also provides the cartridge comprising the transducer and the first, second and third reagents as defined herein. The cartridge is preferably a disposable cartridge.

The present invention will now be described with reference to the following examples which are not intended to be limiting.

EXAMPLES

Example 1

PVDF Film

A poled piezo/pyroelectric polyvinylidene fluoride (PVDF) bimorph film, coated in indium tin oxide was used as the sensing device in the following examples. The indium tin oxide surface was coated with a layer of parylene (of approximate thickness 1 micron) by a vapour phase gas deposition process. This method involved the sublimation and subsequent pyrolysis of a paracyclophane precursor, followed by a free-radical polymerisation on the surface. See WO 2009/141637 for further details. The resulting film was then coated in polystreptavidin solution (200 μg/mL in PBS-10 mmol/L phosphate buffer containing 2.7 mmol/L KCl, 137 mmol/L NaCl and 0.05% Tween) by incubation at room temperature overnight. Polystreptavidin was prepared as described by Tischer et al (U.S. Pat. No. 5,061,640).

Example 2

Materials

Monoclonal antibodies were raised essentially as described in "Monoclonal Antibodies: Properties, Manufacture and Applications" by J. R. Birch and E. S. Lennox, Wiley-Blackwell, 1995, and biotinylated by methods known in the art. Carbon-labelled reporter conjugates were prepared essentially as described by Van Doorn et al. (U.S. Pat. No. 5,641,689).

Example 3

Preparation of the Cartridge

As shown in FIG. 3, a cartridge 14 was fabricated to perform the assay. The cartridge 14 was fabricated from an antibody-coated piezo/pyrofilm 15 supported on a stiffener 16. A pressure sensitive adhesive-coated polyester film 17 die-cut to form three sample chambers 18 was applied to the surface. Provision was made to allow for electrical connections to the top and bottom surfaces of the piezo/pyrofilm 15 in order to detect the charge generated. The cartridge 14 is then formed by sandwiching the above components between a top cover 19, to which a label 20 was applied, and a core 21, seal 22 and bottom cover 23.

Assays were carried out by charging the sample chambers with the sample through the capillary channel in the core 21. The piezo/pyrofilm 15 was irradiated through the holes in the top cover 19 with chopped LED light sequentially with LEDs. For each LED pulse, a voltage is measured across the piezo/pyrofilm 15 using an amplifier and analogue to digital (ADC) converter. The ADC signal is plotted over time.

Example 4

An Immunometric Assay with Controls

Strips of PVDF pyroelectric polymer film were coated in three separate areas with a universal streptavidin coating. The three areas were separated by an adhesive spacer attached to the surface of the sensor, allowing subsequent incubation of different biotinylated antibodies onto each area without cross-contamination of the surfaces. The three surfaces (labelled spot 1, spot 2 and spot 3) were coated with three different antibodies at a concentration of 1 μg/mL for 2 hours, then the surfaces were washed and dried in the presence of sucrose stabiliser.

Spot 1 was coated with a negative control antibody (Abcam, cat. No. AB37358, mouse IgG isotype, biotinylated), spot 2 was coated with a monoclonal anti-TSH antibody and spot 3 was coated with a polyclonal goat anti-mouse antibody which acted as the positive control. Once the strips had been prepared they were assembled into cartridges by removing the release liner from the adhesive spacer and attaching each strip to an injection-moulded piece, the final assembly generating three interconnected chambers. These chambers are discoid, with a diameter of approximately 6 mm and a depth of approximately 200 microns, with an internal volume of around 6 μL. Each cartridge also contained a pre-measured quantity of carbon particles coated in a matching anti-TSH antibody. The carbon particles were dried-down in the cartridge and the cartridge had a mechanism for mixing a liquid sample with these dried reagents to give a homogeneous mixture and then moving that mixture to fill the three chambers as described hereinabove. The final concentration of carbon particles in the sample after mixing was around 0.03%. A range of standards with known concentrations of thyroid stimulating hormone (TSH) in pooled human plasma had been prepared previously and the TSH levels confirmed on a lab analyser. A number (15) of repeat measurements were carried out on each batch of plasma. Each measurement used one of the pre-prepared cartridges; the sample was introduced into the cartridge, then the cartridge was inserted into an instrument designed to measure the electrical output from the pyroelectric film.

Figure 4:
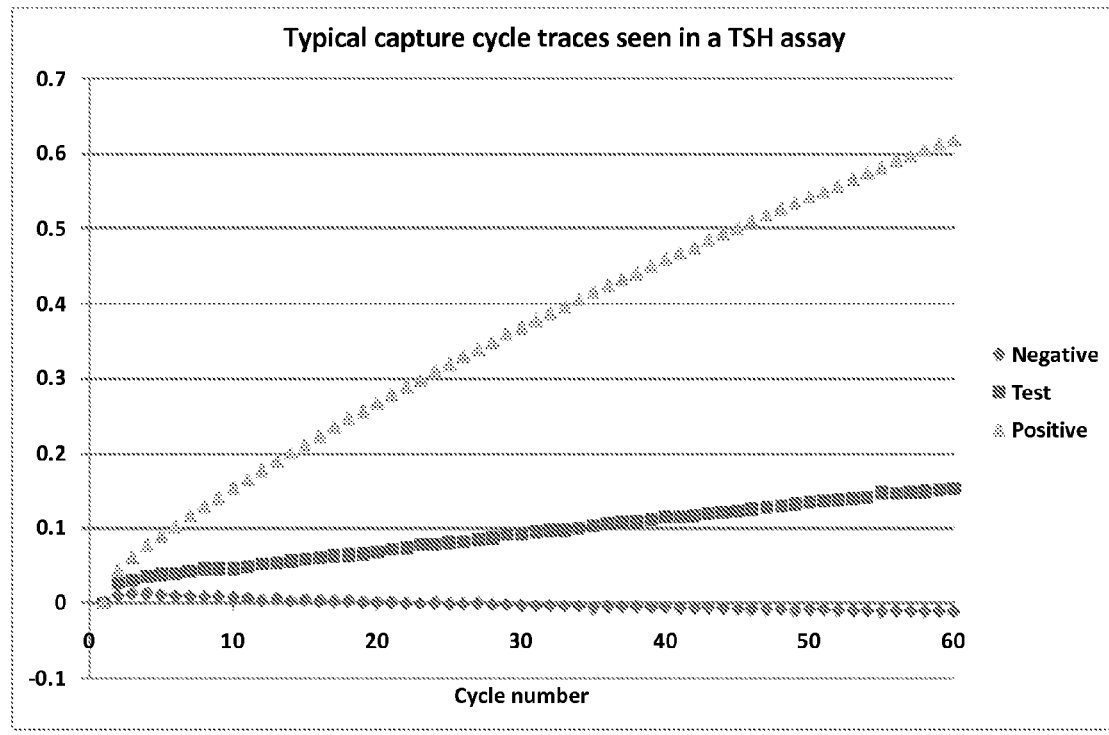
FIG. 4 shows kinetic output in a TSH assay.

The instrument contains a displacement pump that mixes the sample, total volume 30 μL, with the carbon particles and then draws the homogeneous mixture into the chambers. The instrument then illuminates each chamber sequentially over a period of 10 minutes using three high-powered LEDs which pulse on for approximately 10 milliseconds followed by a rest period of 90 milliseconds. The instrument amplifies the electrical output which results from the piezo/pyroelectric sensor upon illumination by the LEDs. The signal is generated by the absorption of light by the carbon particles, followed by the dissipation of heat from the particles into the piezo/pyroelectric sensor. Movement of carbon particles in the chamber, either by direct binding events or unwanted sedimentation effects, led to changes in the electrical output over time. The electrical output was converted into a digital signal and the data were manipulated by an on-board processor to give the output from each chamber as a rate-of-change of signal on an arbitrary digital scale, as shown in FIG. 4.

Approximately 15 repeat measurements were carried out on fresh samples at six different TSH concentrations (0, 1.19, 2.54, 5.24, 10.27 and 24.9 mIU/L), giving approximately 90 independent measurements on 90 cartridges, with three individual outputs from each cartridge. The results are set out in Table 1.

TABLE 1

Individual spot outputs for a TSH immunometric assay

| Conc'n (mIU/L) | Spot 1 | Spot 2 | Spot 3 |
|---|---|---|---|
| 0 | −430.863 | −279.172 | 5136.154 |
| 0 | −296.232 | −307.677 | 5159.129 |
| 0 | −380.79 | −300.006 | 5059.33 |
| 0 | −425.025 | −312.423 | 5185.2 |
| 0 | −350.304 | −201.163 | 5710.019 |
| 0 | −451.426 | −393.822 | 5078.857 |
| 0 | −318.709 | −247.329 | 5412.108 |
| 0 | −299.058 | −191.774 | 6147.915 |
| 0 | −389.291 | −288.363 | 5185.041 |
| 0 | −310.501 | −231.196 | 5758.596 |
| 0 | −327.634 | −250.329 | 5383.575 |
| 0 | −444.138 | −401.929 | 5236.325 |
| 0 | −187.659 | −42.5472 | 6279.682 |
| 0 | −372.483 | −272.93 | 5778.189 |
| 0 | −476.934 | −321.148 | 5225.461 |
| 1.19 | −201.299 | 319.0674 | 6474.52 |
| 1.19 | −481.461 | 19.62871 | 6740.012 |
| 1.19 | 52.09882 | 444.9094 | 6247.385 |
| 1.19 | −53.6086 | 368.0161 | 6393.713 |
| 1.19 | −208.354 | 298.7357 | 6489.471 |
| 1.19 | −308.557 | 153.4231 | 6519.541 |
| 1.19 | −421.218 | 26.96297 | 6350.21 |
| 1.19 | −397.324 | 60.92422 | 5678.382 |
| 1.19 | −209.928 | 296.8847 | 6632.587 |
| 1.19 | −490.974 | 118.0116 | 6837.468 |
| 1.19 | −96.5631 | 384.0316 | 6567.408 |
| 1.19 | 80.95813 | 518.0436 | 7282.508 |
| 2.54 | −188.86 | 604.9265 | 6593.611 |
| 2.54 | −185.094 | 712.4469 | 6208.82 |
| 2.54 | −76.4958 | 796.7206 | 6393.329 |
| 2.54 | −175.388 | 707.2111 | 5886.147 |
| 2.54 | −510.367 | 479.456 | 6125.135 |
| 2.54 | −378.367 | 535.6407 | 5848.956 |
| 2.54 | −265.587 | 539.303 | 6027.396 |
| 2.54 | −93.8712 | 864.2397 | 7658.574 |
| 2.54 | −272.236 | 614.9602 | 6126.295 |
| 2.54 | −188.466 | 497.0843 | 6108.217 |
| 2.54 | −369.535 | 535.506 | 5996.976 |
| 2.54 | −667.347 | 243.174 | 6624.185 |
| 2.54 | −102.437 | 873.7737 | 6793.541 |
| 2.54 | −2.66799 | 972.6595 | 6854.81 |
| 5.24 | −361.523 | 1214.043 | 6143.862 |
| 5.24 | −256.606 | 1292.465 | 7382.176 |
| 5.24 | −293.167 | 1405.229 | 6389.369 |
| 5.24 | −444.116 | 1205.073 | 5563.494 |
| 5.24 | −223.645 | 1366.035 | 6994.522 |
| 5.24 | 395.689 | 2030.376 | 7792.629 |
| 5.24 | −140.611 | 1260.19 | 7006.528 |
| 5.24 | −556.551 | 1173.356 | 6982.299 |
| 5.24 | −503.66 | 1115.905 | 5657.636 |
| 5.24 | −334.672 | 1136.085 | 6463.521 |
| 5.24 | −266.012 | 1116.454 | 5936.568 |
| 5.24 | −736.863 | 917.7635 | 7117.094 |
| 5.24 | −322.266 | 1447.608 | 6757.25 |
| 5.24 | −360.08 | 1224.651 | 6324.574 |
| 5.24 | 4.649984 | 1650.931 | 6305.24 |
| 10.27 | −388.176 | 2481.799 | 6262.157 |
| 10.27 | −254.328 | 2468.424 | 7132.248 |
| 10.27 | −340.157 | 2810.874 | 6898.286 |
| 10.27 | −122.522 | 2352.549 | 6612.683 |
| 10.27 | 525.3487 | 3602.455 | 7480.42 |
| 10.27 | −8.61887 | 2605.52 | 6656.873 |
| 10.27 | −169.62 | 2891.513 | 6812.896 |
| 10.27 | −96.4464 | 3015.453 | 6644.907 |
| 10.27 | −424.326 | 2359.531 | 6447.036 |
| 10.27 | −284.951 | 2364.508 | 6354.903 |
| 10.27 | −82.7793 | 2763.07 | 7170.986 |
| 10.27 | −144.016 | 2706.903 | 6631.797 |
| 10.27 | −282.749 | 2311.535 | 6301.425 |
| 10.27 | −267.324 | 3138.583 | 6741.278 |
| 10.27 | −334.896 | 2456.141 | 5712.895 |
| 24.9 | −69.9036 | 4419.074 | 6317.318 |
| 24.9 | −55.5322 | 4513.409 | 6582.04 |
| 24.9 | −170.798 | 4718.44 | 6472.349 |
| 24.9 | −135.12 | 5067.31 | 6306.789 |
| 24.9 | −97.5404 | 4741.483 | 6936.42 |
| 24.9 | −291.587 | 4297.627 | 6426.706 |
| 24.9 | −220.074 | 4174.713 | 6430.509 |
| 24.9 | −83.8839 | 5296.298 | 7413.253 |
| 24.9 | −227.478 | 4265.226 | 6072.64 |
| 24.9 | −107.843 | 5074.911 | 7078.268 |
| 24.9 | −30.7539 | 4531.776 | 6582.249 |
| 24.9 | 187.5346 | 4842.325 | 6938.801 |
| 24.9 | 100.3582 | 5020.915 | 6818.821 |
| 24.9 | −160.695 | 4690.446 | 7000.276 |
| 24.9 | 543.4999 | 5328.066 | 6631.408 |

The data from Table 1 were manipulated in one of four ways for every cartridge.

Analysis method 1: For each TSH concentration, the output from spot 2 was averaged, and the mean, standard deviation and coefficient of variation (CV) were calculated at each concentration.

Analysis method 2: For each TSH concentration, the output from spot 1 was subtracted from the output in spot 2 (i.e. spot 1 was used as a baseline for the measurement), then the outputs were averaged, and the mean standard deviation and CV were calculated at each concentration.

Analysis method 3: For each TSH concentration, the output from spot 2 was divided by the output from spot 3 (i.e. spot 3 was used as a scaling factor for the measurement), then the mean, SD and CV were calculated at each concentration.

Analysis method 4: For each TSH concentration, the output from spot 1 was subtracted from the outputs in both spot 2 and spot 3 (i.e. both measurements were baseline corrected). Then the baseline corrected measurement in spot 2 was divided by the baseline corrected measurement in spot 3. The mean, SD and CV was then calculated at each concentration.

The CV values, which are a measure of the assay precision, for each of the four data analysis methods are summarised in Table 2.

TABLE 2

Precision measurements for the data analysis methods in an immunometric assay.

| Analyte concentration (mIU/L) | CV | | | |
| | No controls | Spot 1 control | Spot 3 control | Both controls |
|---|---|---|---|---|
| 0 | — | — | — | — |
| 1.19 | 67.64 | 11.75 | 66.19 | 9.30 |
| 2.54 | 30.19 | 9.31 | 26.50 | 9.04 |
| 5.24 | 20.23 | 6.93 | 17.17 | 5.97 |
| 10.27 | 13.43 | 8.77 | 10.15 | 8.37 |
| 24.9 | 7.79 | 6.11 | 6.26 | 5.63 |

Figure 5:
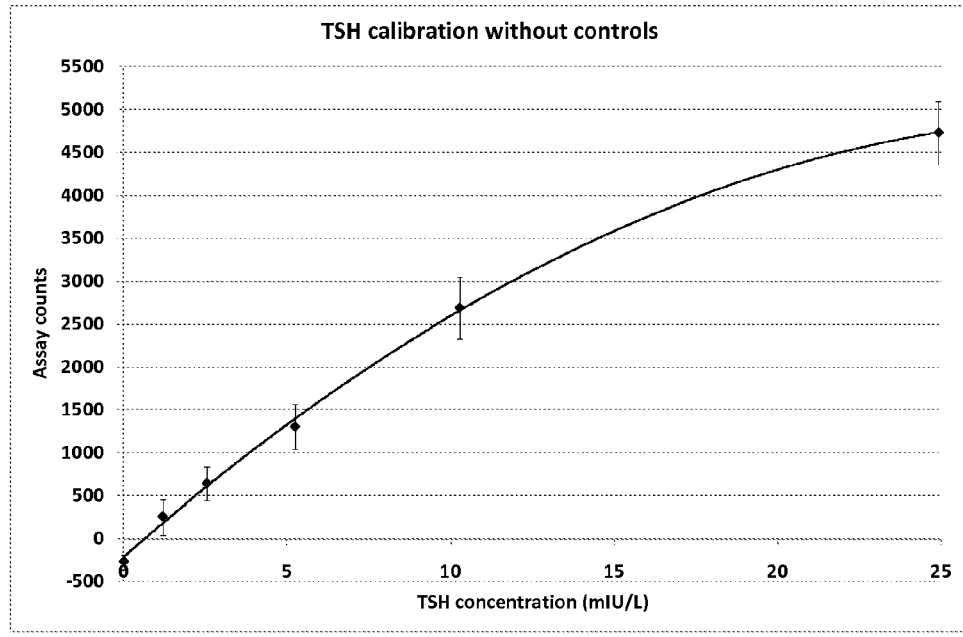
FIG. 5 shows a TSH dose-response curve without using controls.
Figure 6:
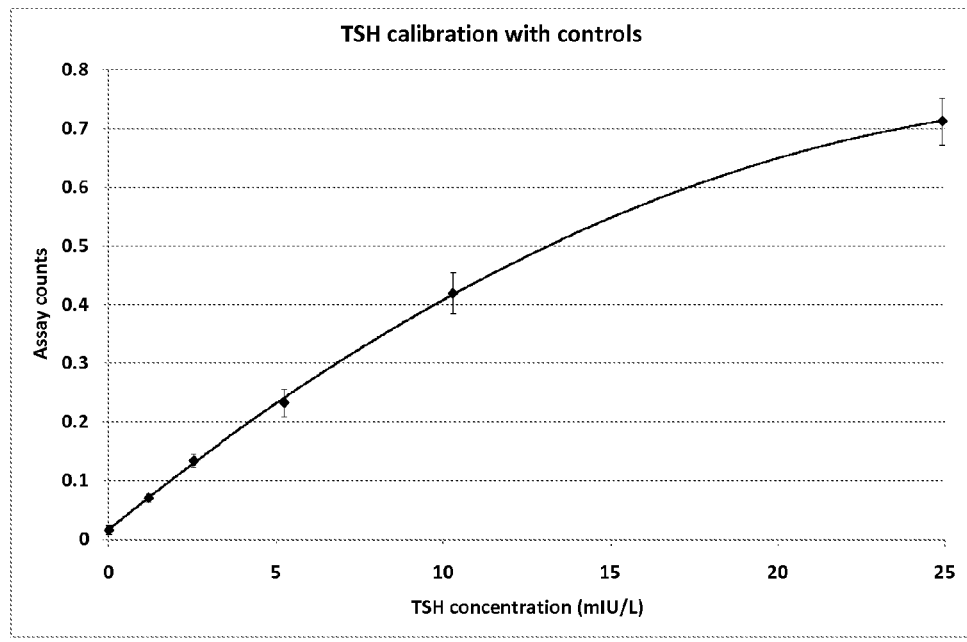
FIG. 6 shows a TSH dose-response curve using positive and negative controls.

It can be clearly seen from Table 2 that the method using both controls gives the lowest CVs at all concentrations. The dose-response curve for the data without using the controls is shown in FIG. 5, and the similar curve using both controls is shown in FIG. 6.

Example 5

A Competitive Assay with Controls

Cartridges were prepared in a similar manner to Example 4, with the same antibody coated in spot 1. Spot 2 was coated in a monoclonal anti-digoxin antibody and spot 3 was coated in a monoclonal anti-fluorescein antibody. In this example the carbon particles were coated in bovine serum albumin (BSA) which had been pre-treated sequentially with digoxigenin N-hydroxysuccinimide and fluorescein isothiocyanate, both at a five-fold molar ratio with respect to the BSA. The BSA-digoxigenin-fluorescein co-conjugate was coated onto the carbon particles by passive adsorption. Digoxigenin is an analogue of digoxin (a cardiac drug), and also binds to the anti-digoxin antibody, although with a lower binding constant than digoxin itself.

Assays were carried out for digoxin levels in pooled plasma that had been previously spiked with digoxin, the levels of which were confirmed on a laboratory analyser. The presence of digoxin in the sample perturbed the binding of the carbon particles to the anti-digoxin antibody in spot 2 of the cartridge. However, digoxin did not interfere with the binding of particles in spot 3 (note that fluorescein is not normally present in human blood samples). Thus spot 3 acted as a control which was independent of the digoxin concentration.

The data from each spot at different digoxin concentrations are given in Table 3.

TABLE 3

Individual spot outputs for a digoxin competitive assay.

| Digoxin concentration (ng/mL) | Spot 1 | Spot 2 | Spot 3 |
|---|---|---|---|
| 0 | −102.874 | 1844.799 | 3147.182 |
| 0 | −99.816 | 1869.622 | 3212.036 |
| 0 | −78.5547 | 2070.562 | 3573.290 |
| 0 | −50.2311 | 1887.335 | 3278.480 |
| 0 | −142.978 | 1944.553 | 3460.877 |
| 0 | −8.78611 | 2034.704 | 3254.373 |
| 0 | −77.914 | 1870.201 | 3145.893 |
| 0 | −72.6845 | 1726.972 | 2991.395 |
| 0 | −101.010 | 1670.998 | 2997.364 |
| 0 | −131.198 | 1945.936 | 3252.535 |
| 1 | −124.4 | 1003.399 | 3088.815 |
| 1 | −91.8898 | 1041.466 | 2867.851 |
| 1 | −134.676 | 949.030 | 2999.202 |
| 1 | −111.209 | 1193.582 | 3435.829 |
| 1 | −141.90 | 947.375 | 2856.940 |
| 1 | −67.0826 | 893.142 | 2743.814 |
| 1 | −142.696 | 830.243 | 2655.475 |
| 1 | −127.007 | 1057.096 | 3066.226 |
| 1 | −185.634 | 874.879 | 2455.256 |
| 1 | −134.237 | 1056.875 | 3218.095 |
| 2 | −113.134 | 637.866 | 3059.223 |
| 2 | −113.204 | 526.357 | 2544.044 |
| 2 | −95.2290 | 577.691 | 2805.049 |
| 2 | −129.459 | 449.852 | 2713.950 |
| 2 | −111.356 | 486.723 | 2709.436 |
| 2 | −130.665 | 780.706 | 3213.256 |
| 2 | −143.007 | 654.540 | 2829.456 |
| 2 | −114.48 | 652.834 | 2985.415 |
| 2 | −84.9757 | 551.450 | 2523.342 |
| 2 | −90.4291 | 538.168 | 2305.948 |
| 4 | −86.9180 | 248.068 | 2707.177 |
| 4 | −147.824 | 273.873 | 2824.922 |
| 4 | −117.217 | 287.317 | 2566.885 |
| 4 | −124.834 | 413.651 | 3144.755 |
| 4 | −53.6179 | 199.637 | 2427.738 |
| 4 | −90.009 | 325.360 | 2903.013 |
| 4 | −24.9996 | 383.641 | 2784.562 |
| 4 | −98.0232 | 249.801 | 2565.939 |

TABLE 3-continued

Individual spot outputs for a digoxin competitive assay.

| Digoxin concentration (ng/mL) | Spot 1 | Spot 2 | Spot 3 |
|---|---|---|---|
| 4 | −134.032 | 150.454 | 2402.826 |
| 4 | −157.303 | 118.269 | 2259.995 |

The data were analysed by the same methods described in Example 4, i.e. without controls, just using control 1, just using control 3, or using both controls. Note that spot 3 was designated the positive control in Example 4, because it mimics the expected response when the system is saturated with analyte. In a competitive assay the dose-response curve is inversely proportional to analyte, so the control in spot 3 mimics the response when there is no analyte present.

It is clearly observed that the precision in the measurement process is much improved by using both controls, as summarised in Table 4.

TABLE 4

Precision measurements for the data analysis methods in a competitive assay.

| | CV | | | |
|---|---|---|---|---|
| Analyte conc. | No controls | Spot 1 control | Spot 3 control | Both controls |
| 0 ng/ml | 6.53 | 6.15 | 3.30 | 2.79 |
| 1 ng/ml | 10.94 | 9.28 | 5.06 | 5.16 |
| 2 ng/ml | 16.62 | 15.07 | 11.30 | 9.30 |
| 4 ng/ml | 35.53 | 23.47 | 27.99 | 14.96 |

Figure 7:
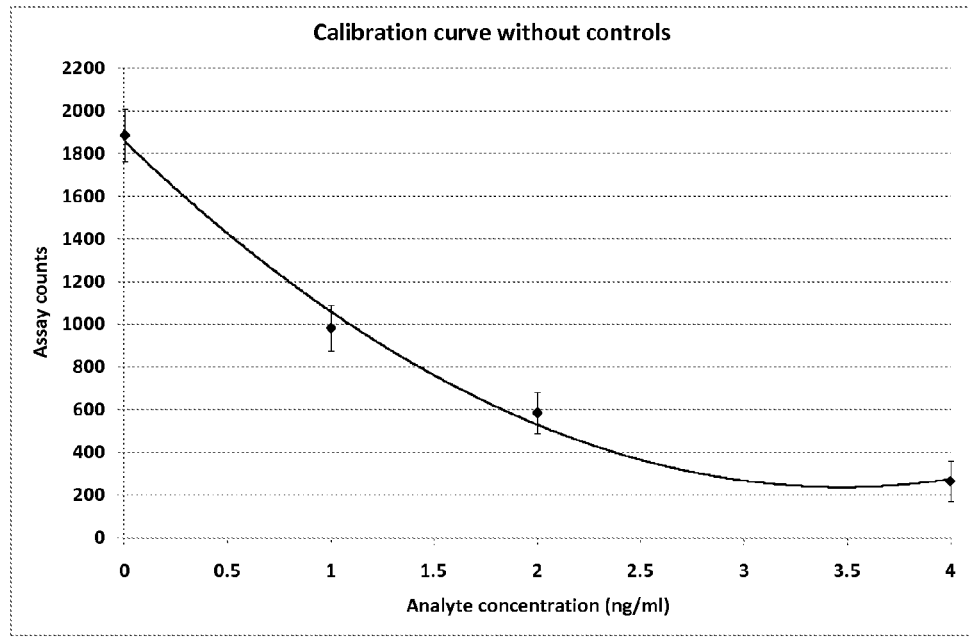
FIG. 7 shows a digoxin dose-response curve without using controls.
Figure 8:
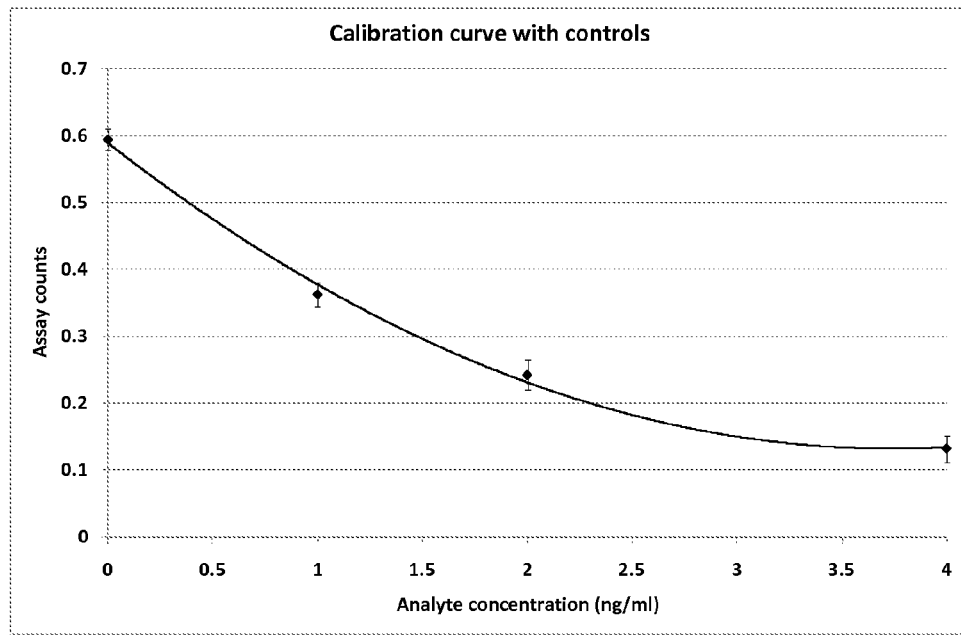
FIG. 8 shows a digoxin dose-response curve using positive and negative controls.

The dose-response graphs with 1 standard deviation error bars for the assay without controls and with both controls are shown in FIGS. 7 and 8, respectively.

Example 6

Figure 9:
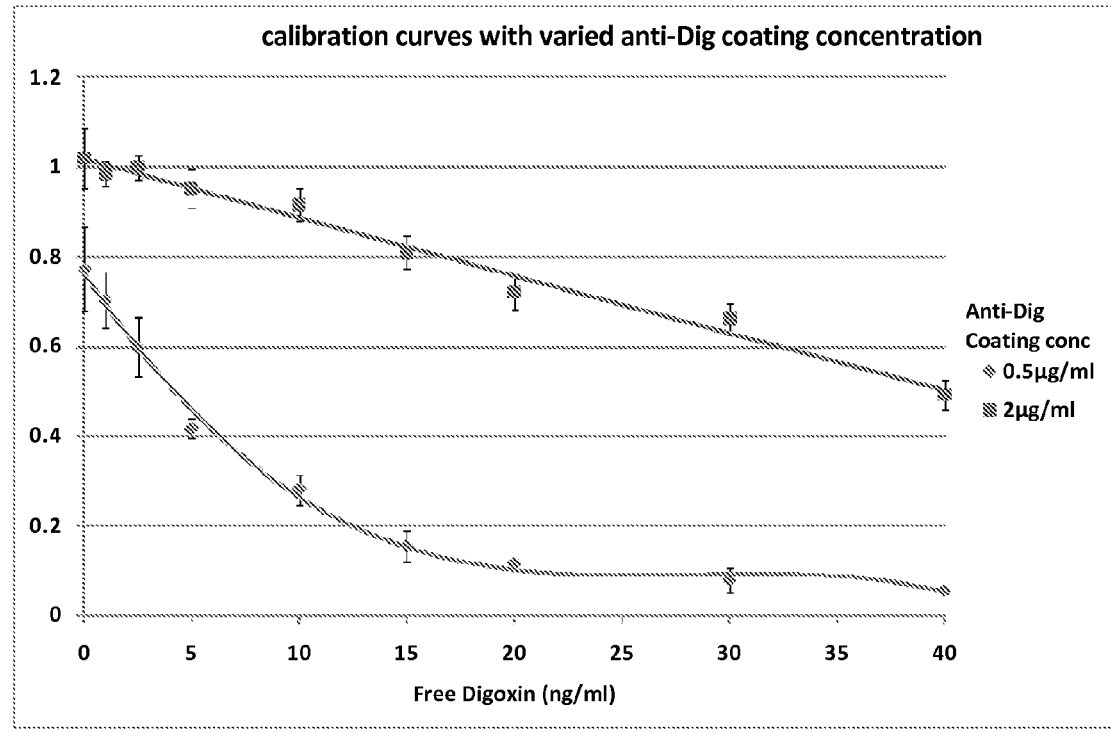
FIG. 9 shows digoxin assay dose-response curves for a cartridge with multiple dynamic ranges.
Figure 10:
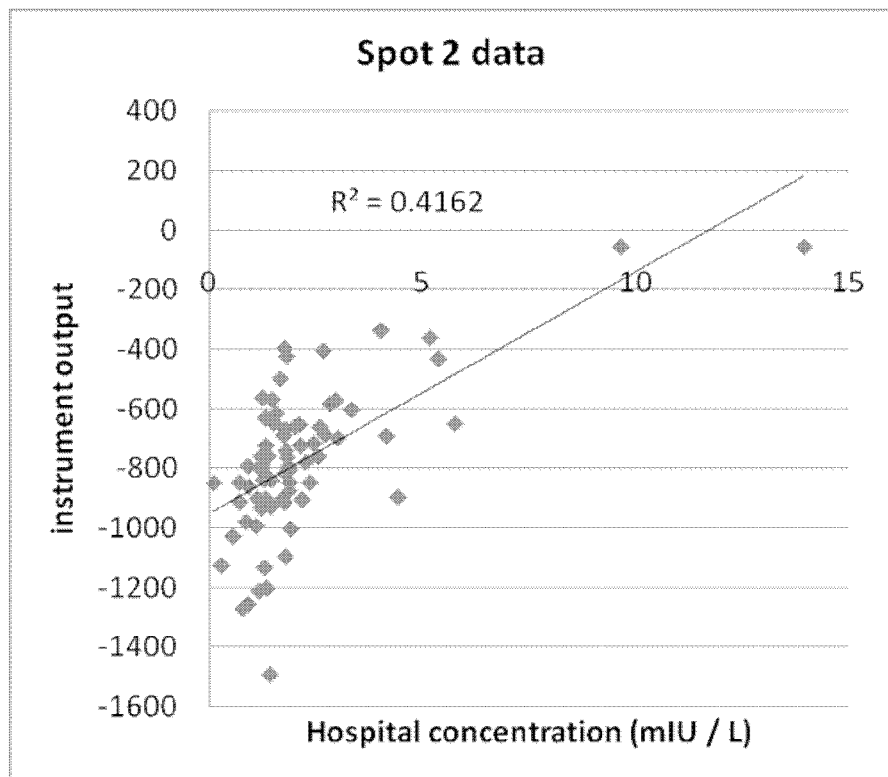
Figure 11:
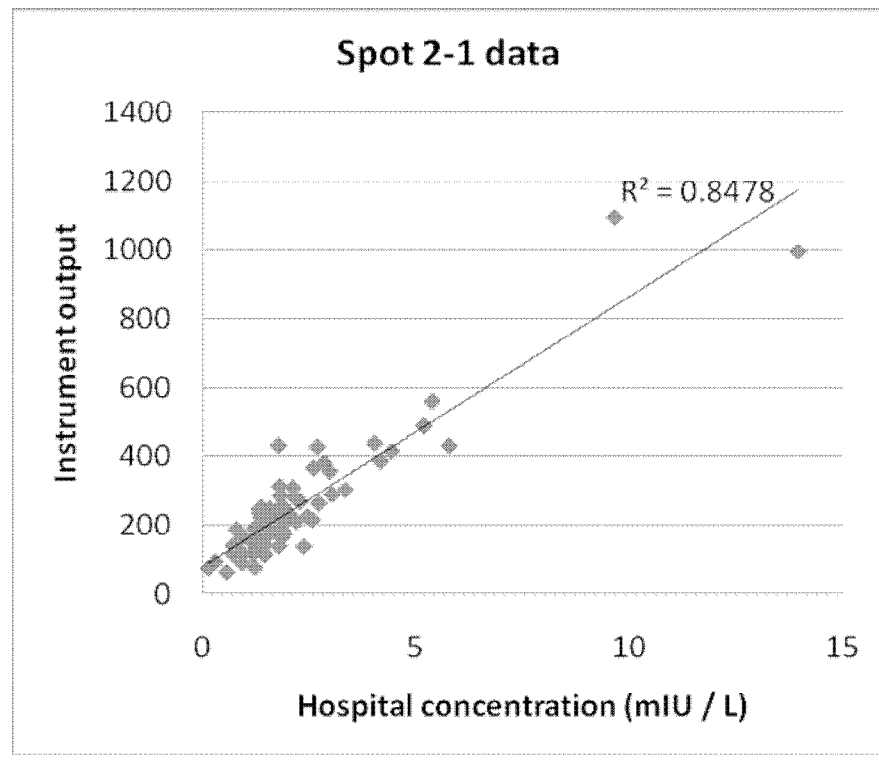
Figure 12:
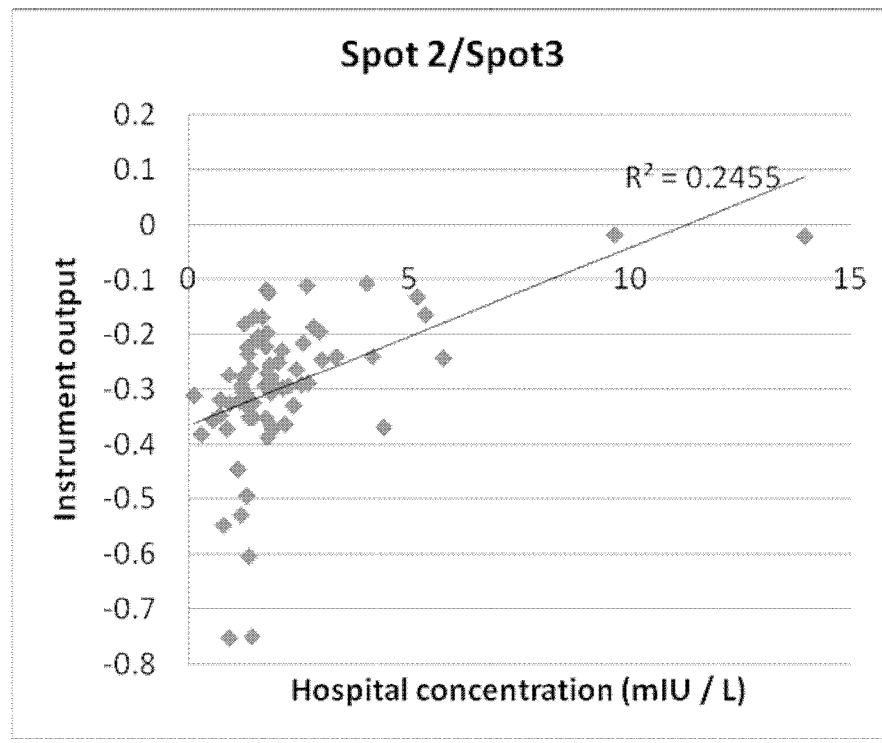

Increased Dynamic Range Achieved by Use of Multiple Measurement Surfaces in Combination with Controls Cartridges were prepared as in Example 5, except that four measurement areas were coated, rather than three. Spots 1 and 4 were the same controls as in Example 5, and spots 2 and 3 were both coated in anti-digoxin antibody, with spot 2 coated in antibody at a concentration of 0.5 μg/mL and spot 3 coated in antibody at 2 μg/mL. Assays for were then run in samples of pooled human plasma which had been spiked with digoxin at a range of concentrations. The data are presented in FIG. 9, showing the mean instrument signal that is observed, along with 1 SD error bars for repeat measurements. The data for spot 2 (0.5 μg/mL anti-digoxin coating) were analysed in conjunction with the two control spots (spots 1 and 4) and the data for spot 3 (1.0 μg/mL anti-digoxin coating) were analysed in conjunction with the two controls (spots 1 and 4) in each cartridge. The methodology of using the control spots was the same as in the Examples 4 and 5 hereinabove, i.e. the output is the baseline-corrected signal in the measurement spot divided by the baseline-corrected signal in the maximum-binding control spot (spot 4 in this instance).

The data are shown in FIG. 9, and it can be clearly observed that the dose-response curve is markedly different for the two anti-digoxin antibody concentrations. For the 0.5 μg/mL coating, the surface becomes saturated with digoxin at lower concentrations, thus the dose response curve is steeper at lower concentrations, giving improved measurements. However, discrimination is lost at concentrations above approximately 15 ng/mL. For the 2 µg/mL coating, the dose-response curve is less steep, so the discrimination is not as good at the low concentrations, but the assay still gives good discrimination at higher concentrations, up to 40 ng/mL. Thus, this assay with controls has the benefit of improved dynamic range over conventional competitive assays.

Example 7

Assay with Controls Across Different Sample Types

A further 100 cartridges were prepared as in Example 4, for the measurement of TSH. These were used as in Example 4, but to measure the TSH levels from approximately 75 healthy human donors. The measurements in this instance were carried out in unseparated whole blood which had been treated with heparin to prevent coagulation of the sample. In parallel, plasma samples were taken from the same donors and these were analysed on a validated laboratory analyser to ascertain the levels of plasma TSH in those donors. The whole blood measurements carried out in the pyroelectric sensor system were manipulated in the same manner as in Example 4, i.e. the outputs were calculated using spot 2, a combination of spots 1 and 2, a combination of spots 2 and 3, or a combination of spots 1, 2 and 3. Since the kinetic measurement was made by diffusion from the plasma component of the whole blood, the output from the instrument was the plasma concentration of the analyte and is independent of the hematocrit of the blood sample.

The measurements according to the four data manipulation methods are shown as scatter plots against the hospital-reported concentrations in FIGS. 10-13. Only data from spot 2 were used in FIG. 10. Data from spot 2 baseline corrected to spot 1 were used in FIG. 11. Data from spot 2 divided by spot 3 were used in FIG. 12. Data from spot 2 baselined to spot 1 expressed as a ratio relative to spot 3 baselined to spot 1 is shown in FIG. 13. The correlation coefficients ($R^2$) for these four methods were 0.42, 0.85, 0.25 and 0.88, respectively, showing that the data manipulation using both controls gave the best correlation with the hospital-measured result.

Examples 4-6 set out hereinabove all show the benefit of improved precision using controls when the sample matrix is a pooled human serum. The improvements must therefore be due to compensating for variability in the cartridge components, instrumentation, environmental conditions and the like, but not due to variability in the sample type. It is well known that human blood and plasma samples are variable in terms of viscosity, hematocrit, interfering factors and general composition. Example 7 shows the benefit of using two controls in improving the accuracy of measurements made across a patient population.

Example 8

Repeat Using Plasma

The same patient samples used in Example 7 were spun down to separate the red cells from the plasma, then the TSH measurement was carried out on the plasma fraction exactly as described in Example 7. The outputs were manipulated exactly as in Example 7, then correlated against the hospital plasma values. The correlation coefficients for spot 2, baselined spot 2, scaled spot 2 and both baselined and scaled spot 2 were 0.61, 0.76, 0.62 and 0.79, respectively.

Examples 7 and 8 indicate that the methodology of using both controls can compensate for variations between different sample types, in additions to other factors such as the components used in the cartridges and/or environmental factors during the measurement.

Examples 4-8 use a similar methodology to provide improved precision and accuracy in either an immunometric or a competitive assay system. There are occasions when it would be beneficial to measure both a small molecule and a large molecule simultaneously in the same sample. For example, one may wish to monitor the plasma concentration of a small molecule drug to ensure that it is in the correct therapeutic range and also measure a protein or hormone to measure the effectiveness of the drug. It would be beneficial to be able to use the same controls for each assay at the same time, in order to limit the amount of sample that is taken or to avoid the necessity of running multiple test in series, rather than in parallel. The following example demonstrates the use of 2 controls which simultaneously improve the performance of a competitive assay and an immunometric assay.

Example 9

Two Assays, One Competitive, the Other Immunometric, Run Simultaneously Using the Same Controls Cartridges were prepared essentially as described in Examples 4-8. These had six individual sensor surfaces which had been coated with a universal streptavidin surface. Spot 1 was then coated with a biotinylated negative control antibody, spot 6 was coated with a goat anti-mouse antibody, spots 2 and 3 were coated with a monoclonal mouse anti-TSH antibody and spots 4 and 5 were coated with a biotinylated digoxigenin molecule. Although there were six areas in this example, the surface areas of each spot were reduced in these cartridges such that the total sample volume remained at 30 µL, a volume that may be obtained from a finger-prick of blood. Spots 2/3 and 4/5 gave repeat measurements of TSH and digoxin, respectively, in this example, although this was not a specific requirement for the assay to function. It should be noted that the format for digoxin measurements in this example was reversed from that presented in Examples 5 and 6, in that the digoxin analogue was bound to the sensor surface and the anti-digoxin antibody was bound to the carbon particles. However, the principle remains the same and the assay could be carried out in either configuration.

A range of pooled plasma standards spiked with known concentrations of solely TSH, solely digoxin or both TSH and digoxin at known concentrations had been prepared previously and the concentrations confirmed on a lab analyser. Separate determinations for TSH and digoxin had to be carried out for each sample on the lab analyser. Repeat (n=10) assays were carried out on each different sample using cartridges that had been prepared with equal concentrations of carbon particles coated with either anti-TSH antibody or anti-digoxin antibody, although it is also possible to co-coat the two antibodies simultaneously onto the same set of particles.

The instrument output was analysed essentially as described in Examples 4 and 5. For TSH, the output from spots 2 and 3 was averaged, and then the data were manipulated using the two control measurements from spots 1 and 6. Spots 4 and 5 were not used. The four analysis methods were the same as described in Example 4. For digoxin, the output from spots 4 and 5 was averaged, and then the data were also manipulated using the same controls measurements from spots 1 and 6. Spots 2 and 3 were not used. The four analysis methods were the same as described in Example 5.

The precision in each repeat measurement using the four data analysis methods is shown in Table 5. It can be clearly observed that improved precision is achieved in all cases by the use of the two control measurements to define the upper and lower limits of the measurement range.

TABLE 5

Precision measurements for the data analysis methods in a multiplex assay in both immunometric and competitive formats

| Analyte concentration | | % CV | | | | | | | |
|---|---|---|---|---|---|---|---|---|---|
| | | TSH | | | | Digoxin | | | |
| TSH (mIU/L) | Digoxin (ng/mL) | No controls | Spot 1 control | Spot 6 control | Both controls | No controls | Spot 1 control | Spot 6 control | Both controls |
| 0 | 0 | — | — | — | — | 4.61 | 4.58 | 4.22 | 3.87 |
| 5.58 | 0 | 28.87 | 20.39 | 24.86 | 17.04 | 7.41 | 6.55 | 5.12 | 4.87 |
| 0 | 1 | — | — | — | — | 7.98 | 7.36 | 10.62 | 6.53 |
| 5.58 | 1 | 14.11 | 12.22 | 13.87 | 11.64 | 6.52 | 5.00 | 8.06 | 4.58 |
| 2.75 | 10 | 27.11 | 12.42 | 31.32 | 11.61 | 144.41 | 22.59 | 140.43 | 21.74 |
| 27 | 2 | 6.72 | 5.75 | 7.41 | 4.06 | 12.82 | 8.40 | 9.85 | 6.81 |

The instrument outputs (as ratiometric signals, using both controls) are shown in FIG. 14, along with 1 standard deviation error bars. The instrument output for either analyte was independent of the presence or absence of the other.

Example 9 indicates that both controls can be used in parallel to improve the performance of a multiplexed competitive/immunometric assay combination.

The invention claimed is:

1. A device for performing an assay on an analyte in a sample comprising:
   a radiation source adapted to generate a series of pulses of electromagnetic radiation;
   a transducer having a pyroelectric or piezoelectric element and electrodes which is capable of transducing energy generated by non-radiative decay into an electrical signal;
   a detector which is capable of detecting the electrical signal generated by the transducer;
   a first reagent proximal to the transducer, the first reagent having a binding site which is capable of binding a labelled reagent proportionally to the concentration of the analyte in the sample, which labelled reagent being capable of absorbing the electromagnetic radiation generated by the radiation source to generate energy by non-radiative decay;
   a second reagent proximal to the transducer, the second reagent having a lower affinity for the labelled reagent under the conditions of the assay than the first reagent; and
   a third reagent proximal to the transducer, the third reagent having a binding site which is capable of binding the labelled reagent, wherein the third reagent has an affinity for the labelled reagent which is less influenced than the first reagent by the concentration of the analyte or the complex or derivative of the analyte; and
   wherein the assay is a homogeneous assay.

2. A device as claimed in claim 1, wherein the second reagent has essentially no affinity for the labelled reagent under the conditions of the assay.

3. A device as claimed in claim 1, wherein the third reagent has an affinity for the labelled reagent which is essentially independent of the concentration of the analyte or the complex or derivative of the analyte.

4. A device as claimed in claim 1, wherein the first, second and third reagents are antibodies.

5. A device as claimed in claim 1, wherein the analyte or the complex or derivative of the analyte is a small molecule.

6. A device as claimed in claim 1, wherein the labelled reagent comprises an antibody raised to the analyte or the complex or derivative of the analyte, the first reagent is an antibody raised to the analyte or the complex or derivative of the analyte, the second reagent is an isotype control antibody, and the third reagent is an anti-species antibody.

7. A device for performing an assay on an analyte in a sample comprising:
   a radiation source adapted to generate a series of pulses of electromagnetic radiation;
   a transducer having a pyroelectric or piezoelectric element and electrodes which is capable of transducing energy generated by non-radiative decay into an electrical signal; a detector which is capable of detecting the electrical signal generated by the transducer;
   a first reagent proximal to the transducer, the first reagent having a binding site which is capable of binding a labelled reagent proportionally to the concentration of the analyte in the sample, which labelled reagent being capable of absorbing the electromagnetic radiation generated by the radiation source to generate energy by non-radiative decay;
   a second reagent proximal to the transducer, the second reagent having a lower affinity for the labelled reagent under the conditions of the assay than the first reagent; and
   a third reagent proximal to the transducer, the third reagent having a binding site which is capable of binding the labelled reagent, wherein the third reagent has an affinity for the labelled reagent which is less influenced than the first reagent by the concentration of the analyte or the complex or derivative of the analyte;
   wherein the device further comprises a chamber for holding a liquid sample containing the analyte or the complex or derivative of the analyte in contact with the transducer; and
   wherein the assay is a homogeneous assay.

8. A device as claimed in claim 1, wherein the device is formed of a reader and a cartridge, in which the cartridge is releasably engageable with the reader, and in which the reader incorporates the radiation source and the detector, and the cartridge incorporates the transducer and the first, second and third reagents.

9. A kit comprising the device as claimed in claim 1 and the labelled reagent.

10. A method for detecting an analyte, or a complex or derivative of the analyte, in a sample comprising the steps of exposing the sample to the device as claimed in claim 1, transducing the energy generated into an electrical signal and detecting the signal.

11. A method as claimed in claim 10, wherein the method is carried out without removing the sample from the transducer between the steps of exposing the sample to the transducer and transducing the energy generated into an electrical signal.

12. A labelled reagent comprising a label capable of absorbing electromagnetic radiation to generate energy by non-radiative decay, a carrier attached to the label, and attached to the carrier, a first member of a first complementary binding pair and a first member of a second complementary binding pair.

13. A labelled reagent as claimed in claim 12, wherein the first member of the first complementary binding pair is selected from therapeutic drugs, drugs of abuse, vitamins and hormones, and the first member of the second complementary binding is selected from BODIPY FL, Dansyl, AlexaFluor 405, AlexaFluor 488, Lucifer Yellow, Rhodamine, Texas Red, biotin and dinitrophenyl aminohexanoic acid.

14. A transducer comprising:
a pyroelectric or piezoelectric element and electrodes;
wherein the transducer is capable of transducing energy generated by non-radiative decay into an electrical signal;
wherein a first reagent is proximal to the transducer, the first reagent having a binding site which is capable of binding a labelled reagent proportionally to the concentration of an analyte in a sample, which labelled reagent being capable of absorbing the electromagnetic radiation generated by a radiation source to generate energy by non-radiative decay;
wherein a second reagent is proximal to the transducer, the second reagent having a lower affinity for the labelled reagent under the conditions of an assay on the analyte in the sample than the first reagent; and
wherein a third reagent is proximal to the transducer, the third reagent having a binding site which is capable of binding the labelled reagent, wherein the third reagent has an affinity for the labelled reagent which is less influenced than the first reagent by the concentration of the analyte or the complex or derivative of the analyte;
wherein the transducer is suitable for being used in a device performing a homogeneous assay.

15. A device as claimed in claim 7, wherein the first, second and third reagents are attached to the transducer via non-covalent bonding.

16. A device as claimed in claim 1, wherein the first, second and third reagents are attached to the transducer via non-covalent bonding.

17. A transducer as claimed in claim 14, wherein the first, second and third reagents are attached to the transducer via non-covalent bonding.

* * * * *